United States Patent [19]

Jessel, Jr. et al.

[11] Plant 5,240

[45] Jun. 5, 1984

[54] CHRYSANTHEMUM PLANT NAMED ASPEN

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 420,902

[22] Filed: Sep. 21, 1982

[51] Int. Cl.[3] ..... A01H 5/00

[52] U.S. Cl. ..... Plt./77

[58] Field of Search ..... Plt./77

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Aspen characterized by its incurved capitulum form; standard capitulum type; white ray floret color; diameter across face of capitulum ranging from 125 to 140 mm. at maturity; uniform nine (9) week photoperiodic flowering response to short days; medium plant height when grown single stem with no long days and a low temperature tolerance of 13° C. (55° F.) for initiation and development under controlled short days with a continuous dark period of 13 to 14 hours.

3 Drawing Figures

The present invention comprises a new and distinct cultivar of *Chrysanthemum morifolium,* Ramat., hereinafter referred to by the cultivar name Aspen.

Aspen is a product of a planned breeding program which had the objective of creating new chrysanthemum cultivars for cut standard mum programs with incurved capitulum form, white ray floret color, nine (9) week flowering response, and having the ability to produce commercially acceptable quality in year round programs. Such traits in combination were in need of improvement in previously available commercial cultivars.

Aspen was originated from a cross made in a controlled breeding program in Barberton, Ohio in 1973. The female parent identified as 68011002 was an unnamed white standard seedling. The male parent of Aspen was an unnamed white standard seedling identified as 7084014 originated from a cross between the cultivar Snowdon and a seedling identified as 63499002.

Aspen was discovered and selected as one flowering plant within the progeny of the stated cross by Walter H. Jessel, Jr. and William E. Duffett on Jan. 31, 1975 in a controlled environment in Barberton, Ohio.

The first act of asexual reproduction of Aspen was accomplished when vegetative cuttings were taken from the initial selection in April 1975 in a controlled environment in Barberton, Ohio by a technician working under formulations established and supervised by William E. Duffett.

Horticultural examination of selected units initiated August 1977 has demonstrated that the combination of characteristics as herein disclosed for Aspen are firmly fixed and are retained through successive generations of asexual reproduction.

Aspen has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Aspen which in combination distinguish this chrysanthemum as a new and distinct cultivar:

(1) Incurved capitulum form;
(2) Standard capitulum type;
(3) White ray floret color with minimum color oxidation;
(4) Diameter across face of capitulum ranging from 125 to 140 mm. at maturity;
(5) Uniform nine (9) week photoperiodic flowering response to short days;
(6) Medium plant height (requiring 2 to 3 long day weeks prior to short days to attain a flowered plant height of 80 to 90 cm. for November through April flowerings); and
(7) Low temperature tolerance of 13° C. (55° F.) for initiation and development when grown in single stem cut standard programs with a continuous dark period of 13 to b 14 hours.

The accompanying photographic drawings show typical inflorescence and foliage characteristics of Aspen, with the colors being as nearly true as possible with illustrations of this type. Sheet 1 is a color photograph of Aspen grown as a single stem cut standard. Sheet 2 is a black and white photograph showing the top and bottom of leaves of Aspen at three stages of growth. Sheet 3 is a black and white photograph of three views of the inflorescence of Aspen.

Of the many commercial cultivars known to the present inventors, the most similar in comparison to Aspen is Albatross. Reference is made to attached Chart A which compares certain characteristics of Aspen to those same characteristics of Albatross.

In comparison to Albatross, Aspen has a larger diameter across face of capitulum and taller plant height. The ray floret color, capitulum form, capitulum type and flowering response are similar to those same characteristics of Albatross.

In the following description, color references are made to The Royal Horticultural Society Color Chart. The color values were determined between 10:30 and 11:00 A.M. on June 30, 1982 under 150 foot-candle light intensity at Salinas, Calif.

Classification:

*Botanical.*—Chrysanthemum morifolium, Ramat., cv ASPEN.

*Commercial.*—Cut white standard.

INFLORESCENCE

A. Capitulum:

*Form.*—Incurved.

*Type.*—Standard.

*Diameter across face.*—125 to 140 mm.

B. Corolla of Ray Florets:

*Color (general tonality from a distance of three meters).*—White.

*Color (abaxial).*—155D.

*Color (adaxial).*—155D.

C. Corolla of disc florets:

*Color (mature).*—6D.

*Color (immature).*—154B.

D. Reproductive organs:

*Androecium.*—Present disc florets only; abundant pollen during high light periods; scant pollen during low light and/or low temperature conditions.

*Gynoecium.*—Present both ray and disc florets.

PLANT

A. General appearance:

*Height.*—60 to 70 cm., as a flowering plant from a rooted cutting, with no long days for November through April flowerings and maintaining a minimum nightly 14 hour continuous dark period.

B. Foliage:

*Color (abaxial).*—147A.

*Color (adaxial).*—147B.

*Shape.*—Deeply lobed and coarsely serrated.

CHART A

COMPARISON OF ASPEN AND ALBATROSS

| CULTIVAR | RAY FLORET COLOR | CAPITULUM FORM AND TYPE | DIAMETER ACROSS FACE OF CAPITULUM |
|---|---|---|---|
| ASPEN | WHITE | INCURVED STANDARD | 125 to 140 mm. |
| ALBATROSS- | WHITE | INCURVED STANDARD | 115 to 125 mm. |

| CULTIVAR | PLANT HEIGHT | FLOWER RESPONSE PERIOD |
|---|---|---|
| ASPEN | MEDIUM 60 to 70 cm. | 9 week |
| ALBATROSS | SHORT 45 to 55 cm. | 9 week |

COMPARISONS MADE OF PLANTS GROWN AS SINGEL STEM CUT STANDARDS WITH NO LONG DAYS IN SALINAS, CALIFORNIA

We claim:

1. A new and distinct plant of *Chrysanthemum morifolium,* Ramat., known by the cultivar name of Aspen, as described and illustrated, and particularly characterized as to uniqueness by the combined characteristics of incurved capitulum form; standard capitulum type; white ray floret color; diameter across face of capitulum ranging from 125 to 140 mm. at maturity; uniform nine (9) week flowering response; medium plant height when grown single stem with no long days and a low temperature tolerance of 13° C. (55° F.) for initiation and development under controlled short days with a continuous dark period of 13 to 15 hours.

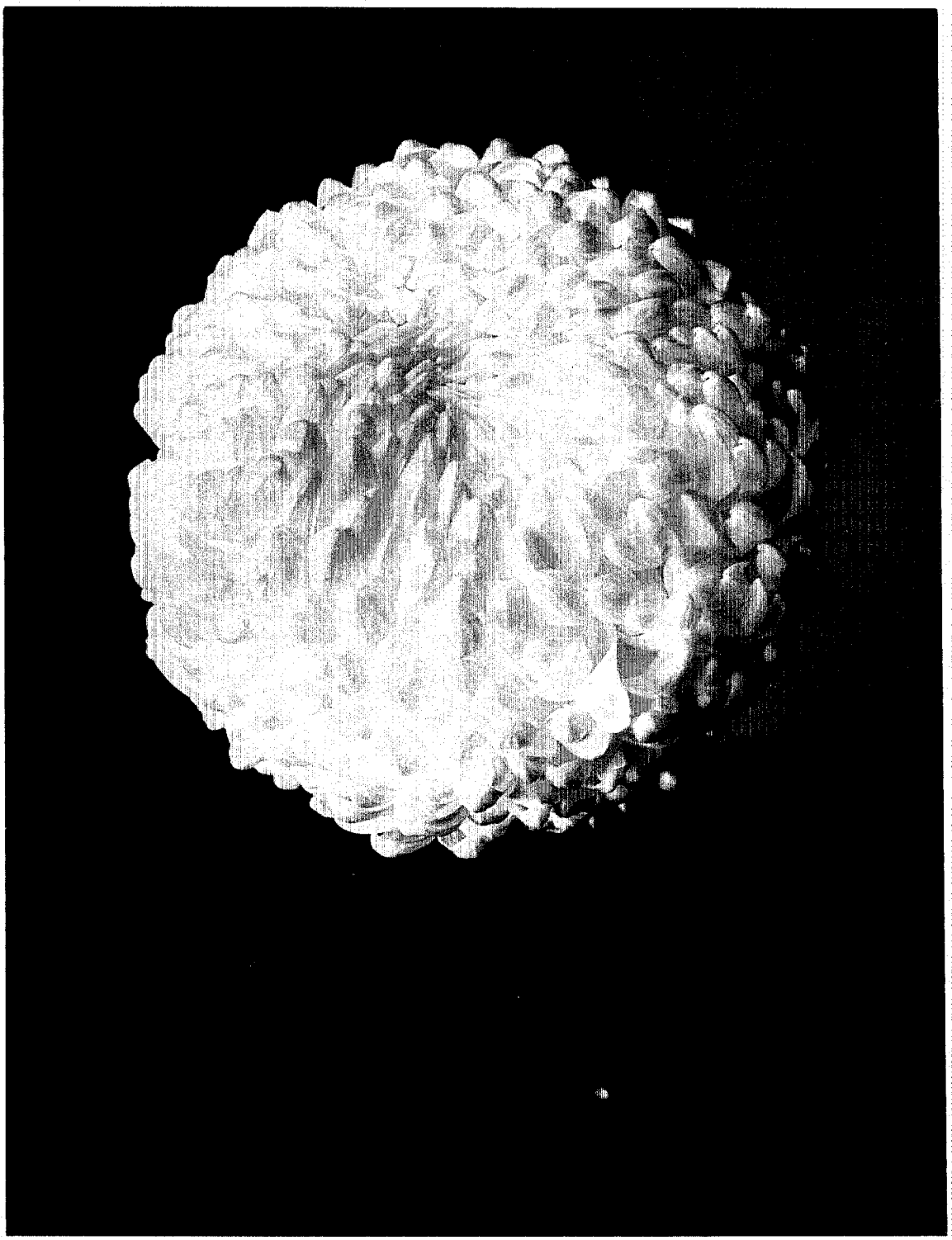

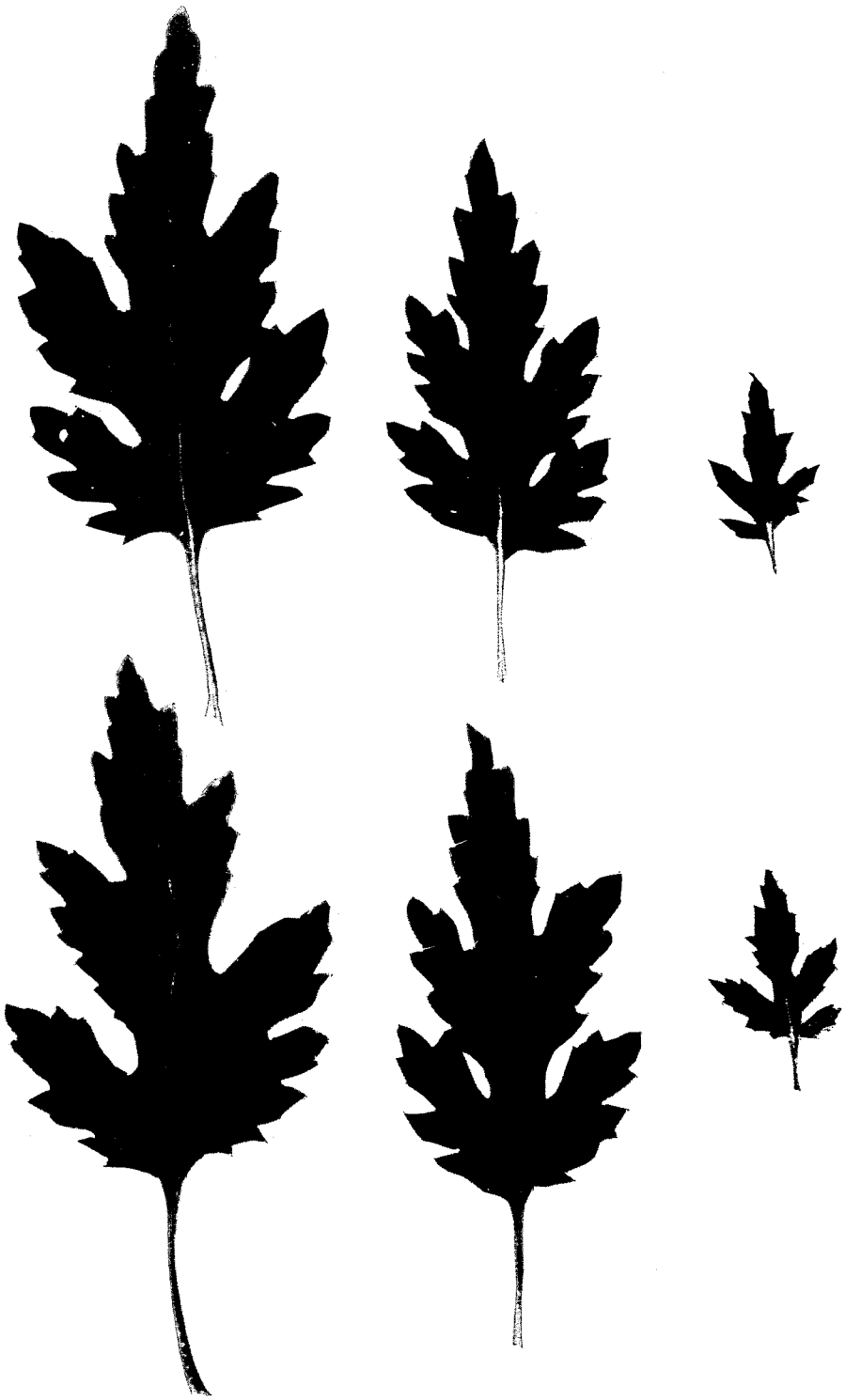

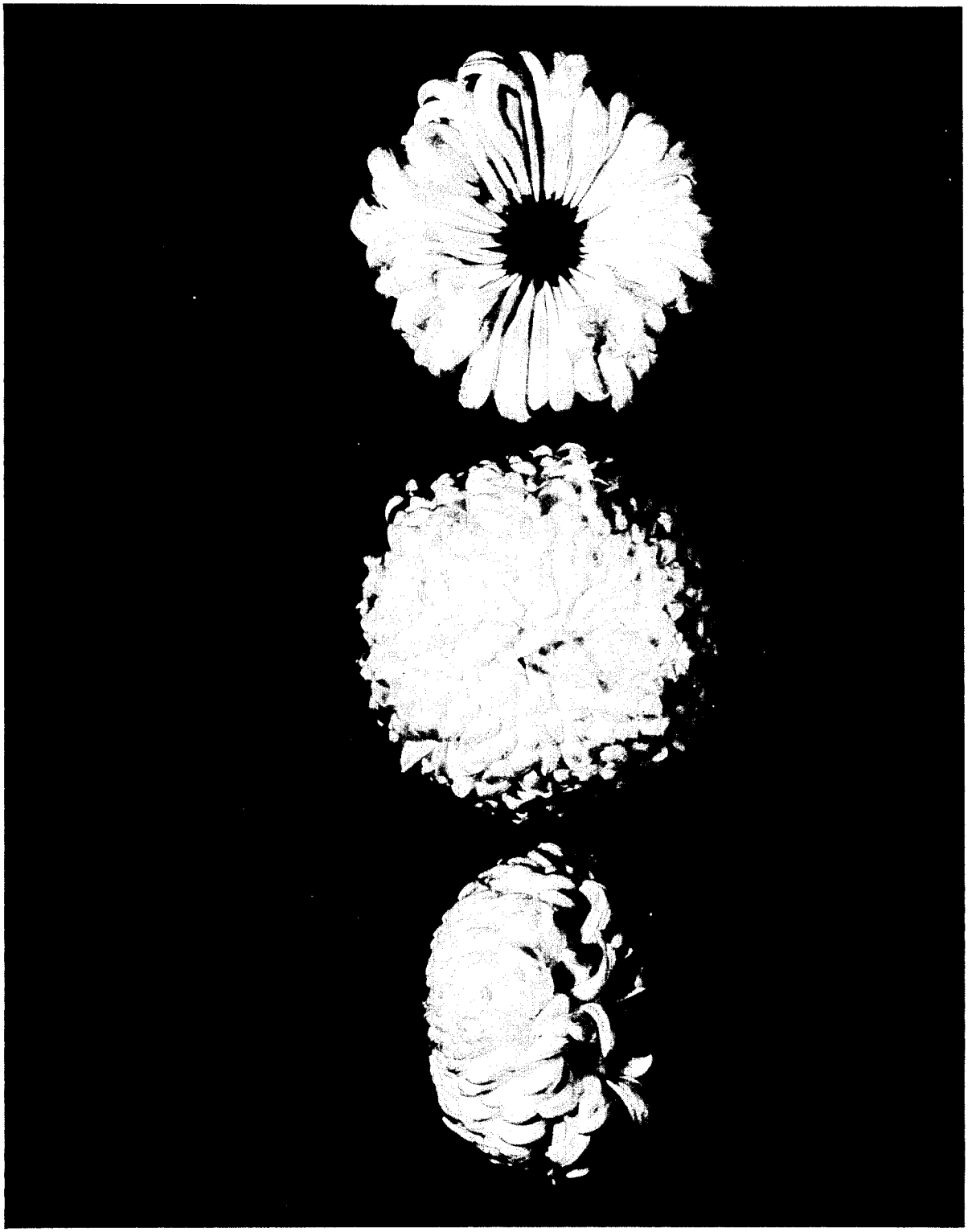

* * * * *